(12) United States Patent
Krietzman

(10) Patent No.: US 10,299,515 B2
(45) Date of Patent: May 28, 2019

(54) DYNAMIC ZONED VAPORIZER

(71) Applicant: Mark Krietzman, Palos Verdes Estates, CA (US)

(72) Inventor: Mark Krietzman, Palos Verdes Estates, CA (US)

(*) Notice: Subject to any disclaimer, the term of this patent is extended or adjusted under 35 U.S.C. 154(b) by 0 days.

(21) Appl. No.: 15/898,629

(22) Filed: Feb. 18, 2018

(65) Prior Publication Data

US 2018/0168237 A1 Jun. 21, 2018

Related U.S. Application Data

(63) Continuation-in-part of application No. 15/045,442, filed on Feb. 17, 2016, now Pat. No. 9,894,936.

(60) Provisional application No. 62/551,234, filed on Aug. 29, 2017, provisional application No. 62/270,557, filed on Dec. 21, 2015, provisional application No. 62/208,786, filed on Aug. 23, 2015, provisional application No. 62/184,396, filed on Jun. 25, 2015, provisional application No. 62/127,817, filed on Mar. 3, 2015, provisional application No. 62/116,926, filed on Feb. 17, 2015.

(51) Int. Cl.
*A24F 47/00* (2006.01)
*A24B 15/16* (2006.01)
*H05B 3/42* (2006.01)
*A61M 21/02* (2006.01)
*A61M 15/06* (2006.01)
*A61M 15/08* (2006.01)
*A61M 11/04* (2006.01)
*A61M 21/00* (2006.01)

(52) U.S. Cl.
CPC ............ *A24F 47/008* (2013.01); *A24B 15/16* (2013.01); *A61M 11/042* (2014.02); *A61M 15/06* (2013.01); *A61M 15/08* (2013.01); *A61M 21/02* (2013.01); *H05B 3/42* (2013.01); *A61M 2021/0016* (2013.01); *A61M 2205/3368* (2013.01); *A61M 2205/3569* (2013.01); *A61M 2205/3592* (2013.01); *A61M 2205/3653* (2013.01); *A61M 2205/505* (2013.01); *A61M 2205/581* (2013.01); *A61M 2205/582* (2013.01); *A61M 2205/583* (2013.01); *A61M 2205/8206* (2013.01); *H05B 2203/021* (2013.01); *H05B 2203/022* (2013.01)

(58) Field of Classification Search
CPC .................................................... A24F 47/008
See application file for complete search history.

(56) References Cited

U.S. PATENT DOCUMENTS

2016/0255879 A1* 9/2016 Paprocki .............. H05B 1/0291
2016/0278436 A1* 9/2016 Verleur ................ A24F 47/008

* cited by examiner

*Primary Examiner* — Ross N Gushi

(57) ABSTRACT

Disclosed herein are methods and systems to vaporize or release organic material from plant material containing the organic material and the like, including utilizing zoned heating of a common chamber. A controller in signal communication with two or more heating elements each adjacent to a zone to be heated controls at least the heating of the elements. The chamber may have a removable floor portion.

17 Claims, 16 Drawing Sheets

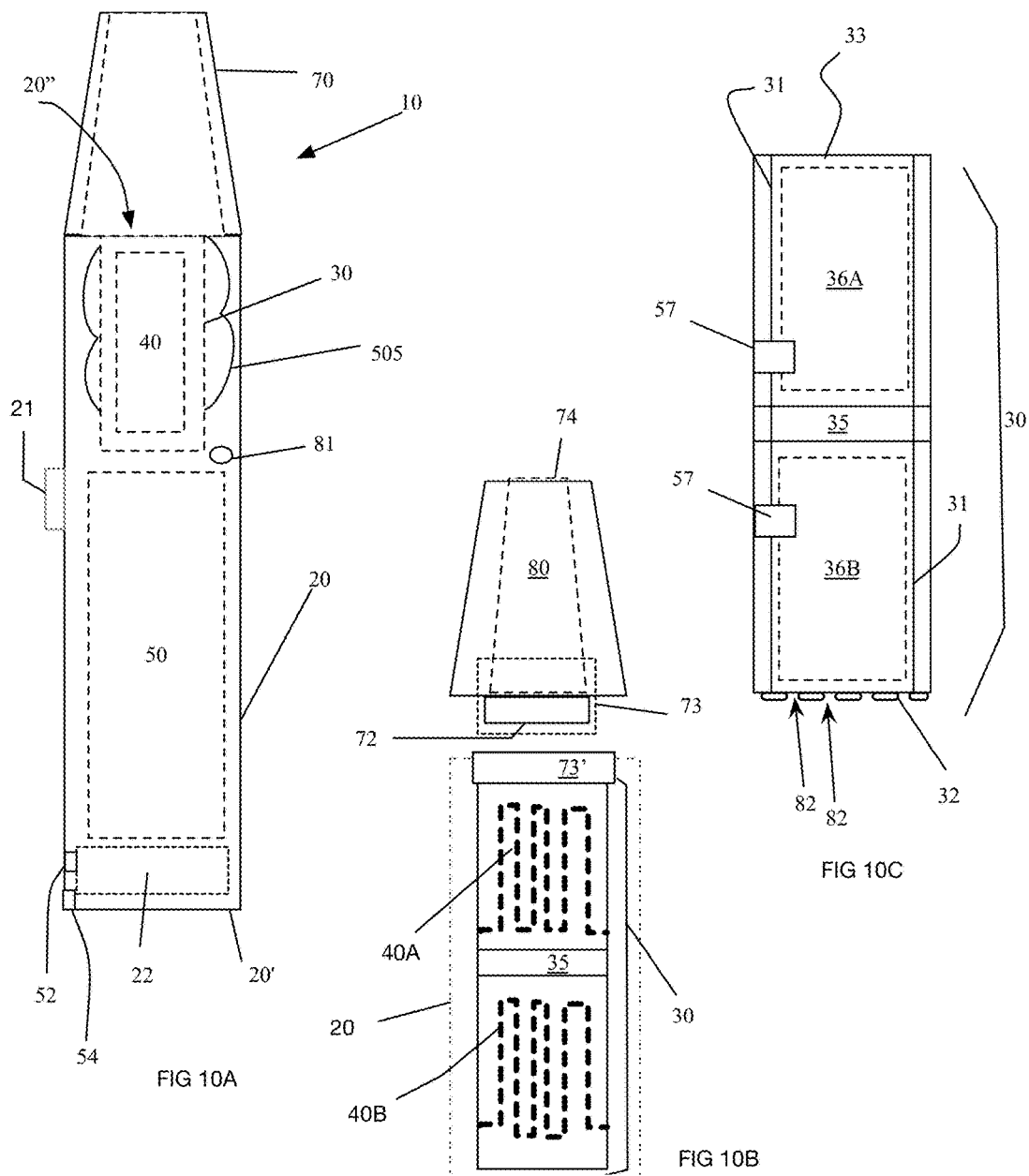

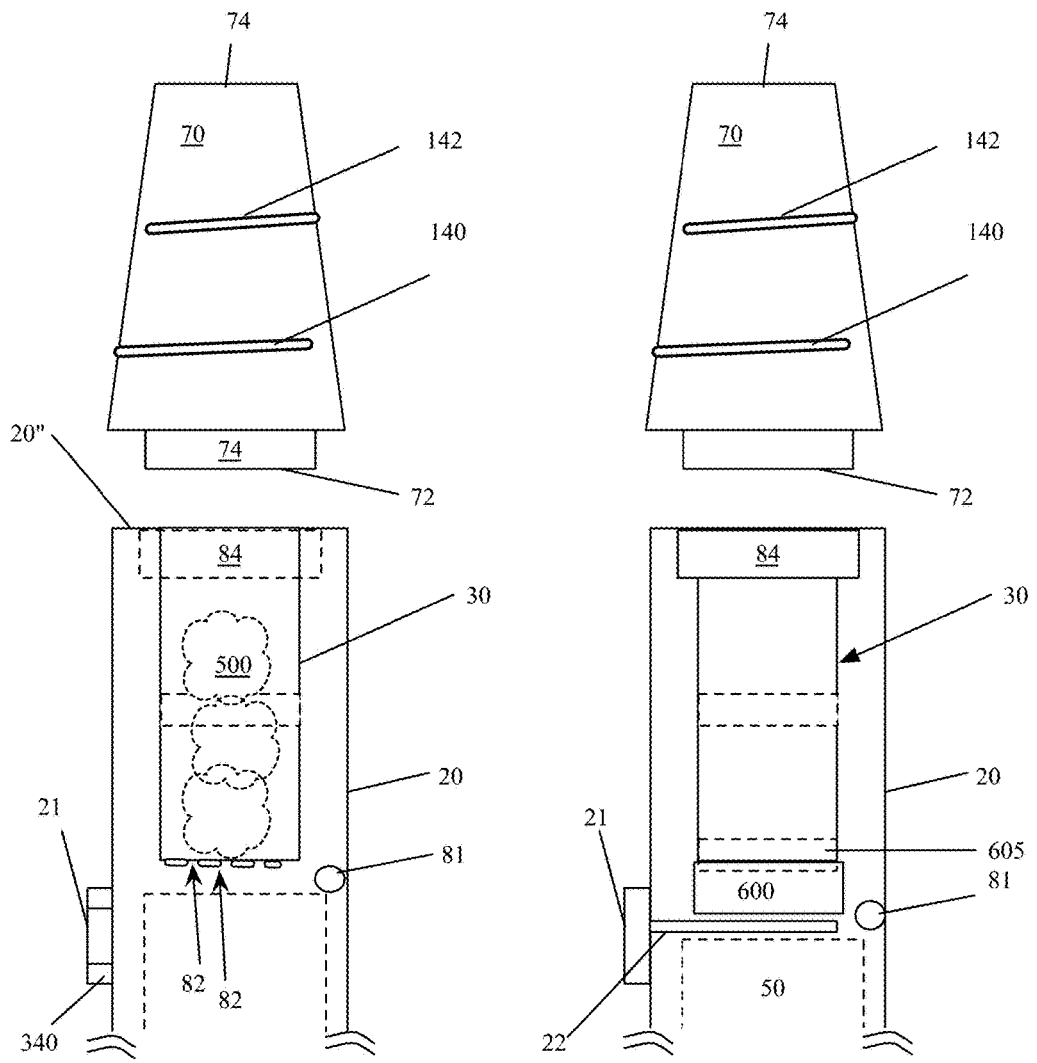

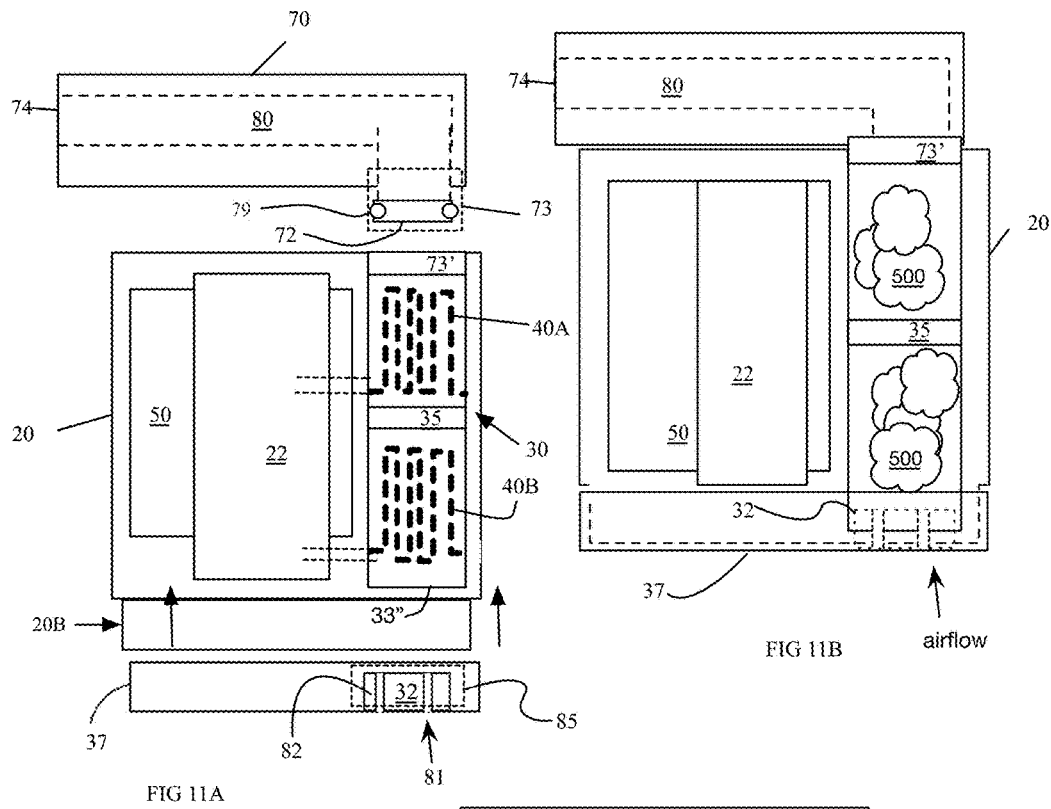
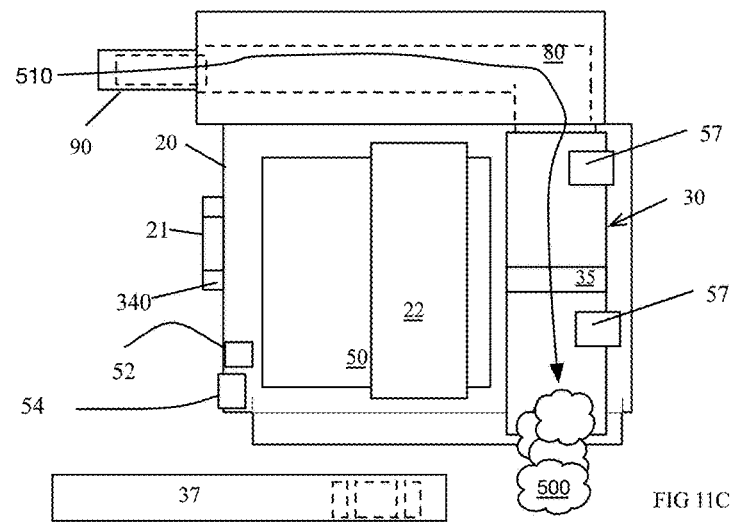

DYNAMIC ZONED VAPORIZER

RELATED APPLICATION

This application is a continuation in part of U.S. ("U.S.") Utility application Ser. No. 15/045,442 which claims the benefit of U.S. Provisional Patent Applications Ser. No. 62/116,926 entitled CARTRIDGE AND HEATER filed on 17 Feb. 2015; Application Ser. No. 62/127,817 entitled MULTI ZONE VAPORIZER filed on 3 Mar. 2015; Application Ser. No. 62/184,396 entitled VAPORIZER DEVICE AND METHOD 25 Jun. 2015; Application Ser. No. 62/208,786 entitled VAPORIZER CARTRIDGE AND HEATER 23 Aug. 2015; Application Ser. No. 62/270,557 entitled THIN CONVECTION VAPORIZER filed 21 Dec. 2015 the disclosures of each of the above referenced applications are incorporated by reference herein in their entirety as if fully set forth herein.

This application also claims the benefit of U.S. Provisional Patent Applications Ser. No. 62/551,234 entitled ZONED VAPORIZERS filed 29 Aug. 2017, the disclosure of which is also incorporated by reference herein in their entirety as if fully set forth herein.

BACKGROUND OF THE DISCLOSURE

Field of the Disclosure

The present disclosure relates generally to heating system and device for aromatherapy which release organic residue from essential oils, extracts and plant based material upon application of heat without combustion.

Related Art

Vaporizer for plant based materials and essential oils and exist. Vaporizers which allow a fluid gas containing the vapor and other residues to follow a fluid pathway from source of vapor to user inhalation exist. Cannabis and other botanicals have been known in the art to be vaporized or burned to release organic material in the form of inhalable material. Vaporizing at correct temperatures can boil off the oils for inhalation without combusting the plant material.

Vaporizer for plant based materials and essential oils and exist. Vaporizers allow aromatherapy or inhalation. Vaporizers which allow inhalation from a fluid pathway whereby gas containing the vapor without combustion by products through a fluid pathway from source of vapor to exists. Herbs and botanicals have been known in the art to be vaporized or burned to release organic material in the form of inhalable material.

Lavender vaporizes at 260° F. Tobacco vaporizes between 257° F. to 302° F.; Green tea vaporizes between about 175° C. to 185° C.; Valerian vaporizes at about 235° C.; Chamomile used to aid in the relief of anxiety vaporizes at about 380° F.; Peppermint vaporizes at about 255° F. Peppermint is also known to ease symptoms of allergies and asthma, in addition to alleviating some of the side effects that come along with the common cold or a sinus infection. Cannabis, has a range at which it can be heated to release different cannabinoids as vapor without burning the organic material. From below 200 F to about 430 F.

*Cannabis sativa* contains over 421 different chemical compounds, including over 60 cannabinoids. Cannabinoid plant chemistry is far more complex than that of pure THC, and different effects may be expected due to the presence of additional cannabinoids and other chemicals. Eighteen different classes of chemicals, including nitrogenous compounds, amino acids, hydrocarbons, carbohydrates, terpenes, and simple and fatty acids, contribute to the known pharmacological properties of cannabis.

Heating a chamber loaded with organic material may, in some instances, overheat at least portions thereof and therefore combust, overheat or otherwise release unwanted items which may include carcinogens and chemicals into the vapor.

It is therefore a desideratum to have a device, method and or system wherein such heating is better managed.

Heating a chamber containing with organic material may, in some instances, overheat at least portions thereof and therefore combust, overheat or otherwise release unwanted items which may include carcinogens and chemicals into the vapor.

Heating a large volume of material, to achieve vaporization temperature in under 2 minutes, for approximately 3 $cm^3$ in a small portable device would eliminate the need to refill said material as often.

It is therefore a desideratum to have a device, method and or system wherein such heating is achieved in a small portable package.

DESCRIPTION

Aspects of vaporizer systems and methods disclosed include a controller that manages heating of a zone at a selected exposure temperatures (SET) to vaporize organic compounds in a portion of material in the containment area in a chamber, and in accordance with one of variable, preselected and fixed times. In some instances the controller prohibits heating when a zone or region has already been heated for a predetermined time. In some instances the controller prohibits heating until chamber has been refilled. In some instances the controller may accept a user override to allow reheating of a chamber, a zone within the chamber or to heat multiple zones simultaneously.

Aspects of aromatherapy vaporizer systems and methods disclosed include a controller; a battery power supply; an on/off switch; a heating chamber including at least an open top surrounded by an annular wall and having an open bottom; a floor; vents connected to air intakes in at least one of the annular wall and the floor; at least one heating element in thermal contact with at least a portion of the heating chamber; a resealable lid (70) which reversibly mate with the heating chamber; a fluid pathway inside the lid from the top of the open chamber to an interface for inhalation; wherein each heating element is separately controlled by the controller; wherein the removable floor closes off a portion of the bottom of the heating chamber; and, wherein the power supply is electrically connected to the heating element and the controller via the on/off switch. In some instances the floor is removable from the open bottom of the chamber.

Aspects of aromatherapy vaporizer systems and methods disclosed include a controller; a battery power supply; an on/off switch; a heating chamber including at least an open top surrounded by an annular wall and having an open bottom; a floor; vents connected to air intakes in at least one of the annular wall and the floor; at least two or more heating elements each in thermal contact with a portion of the heating chamber; a divider between the portions of the heating chamber; a resealable lid (70) which reversibly mate with the heating chamber; a fluid pathway inside the lid from the top of the open chamber to an interface for inhalation; wherein each heating element is separately controlled by the controller; wherein the removable floor closes off a portion of the bottom of the heating chamber; and, wherein the power supply is electrically connected to the heating elements and the controller via the on/off switch. The divider may be an insulator. The divider In some instances the floor is removable from the open bottom of the chamber.

Aspects of aromatherapy vaporizer systems and methods disclosed include a controller; a battery power supply; an on/off switch; a heating chamber including at least an open top surrounded by an annular wall and having an open bottom; a floor; vents connected to air intakes in at least one of the annular wall and the floor; at least two or more heating elements each in thermal contact with a portion of the heating chamber; a divider between the portions of the heating chamber; at least one temperature sensor in signal communication with the controller; a resealable lid (70) which reversibly mate with the heating chamber; a fluid pathway inside the lid from the top of the open chamber to an interface for inhalation; wherein each heating element is separately controlled by the controller; wherein the removable floor closes off a portion of the bottom of the heating chamber; and, wherein the power supply is electrically connected to the heating elements and the controller via the on/off switch. The divider may be an insulator. In some instances the floor is removable from the open bottom of the chamber.

In some of the above exemplars the at least one temperature sensor is connected to the controller and the controller in response to temperature sensor measurements adjusts the amount and/or timing of electricity provided to a turned-on heating. In some instance an illumination communications system is controlled by the controller.

In above exemplars the controller may at least one of measure the amount of time a heating element is at a predetermined range of temperature and measures when a predetermined time is met. In some instances the controller determines if a zone or heating element has measured at a predetermined temperature for a predetermined amount of time. A sensor may be included which measures one or more of when the lid is place on the chamber and when the lid is removed from the chamber.

In above exemplars the controller may at least one of controls heat to each zone heating element based on one of a fixed time, a variable time and a selected time.

Aspects of aromatherapy vaporizer systems and methods disclosed include encasing a generally tubular heating chamber having two or more heating zones each zone having a heating element configured to receive electrical power from one at least one of a battery power supply and controller; temporarily and partially closing off an open bottom of the tubular chamber with a floor; placing material in to an open top of the chamber; covering the open top of the tubular chamber with a lid having a fluid pathway from the open top through the lid; wherein each heating element is separately controlled by the controller; wherein the power supply is electrically connected to the heating elements and the controller via a user activated on/off switch controls the supply of power to each of the heating elements; and, wherein the controller supplies sufficient electrical power to the heating element to vaporize at least some of the essential oils on material. In some instances the controller will not provide electricity for a heating element until such time as the lid is covering the open top of the chamber. In some instances controller stops providing electrical power to a heating element after a predetermined amount of time. In some instances the controller will not provide heating for any heating element after the time is met until such time as the lid has been removed from the chamber.

In above exemplars the controller may adjust at least one temperature sensor in signal communication with the controller; and, wherein the controller in response to temperature sensor measurements adjusts the amount and/or timing of electricity provided to a heating element.

Aspects of aromatherapy vaporizer systems and methods disclosed include using at least two separate heating elements to selectively heat up different portions of a common chamber; selectively controlling the heating elements by a controller; and, wherein at least one of the temperature and the time of heating is controlled by the controller. In some instances placing at least one temperature sensor in signal communication with the controller and wherein the controller in response to temperature sensor measurements adjusts the amount and/or timing of electricity provided to a turned on heating element. In some instances communicating via illumination if the temperature of at least a portion of the common chamber is at a predetermined temperature Aspects of vaporizer methods include using at least two separate heating elements to selectively heat up different portions of a common chamber; selectively controlling the heating elements by a controller; and, wherein at least one of the temperature and the time of heating is controlled by the controller. The methods may further include connecting at least one temperature sensor to the controller and wherein the controller in response to temperature sensor measurements adjusts the amount and/or timing of electricity provided to a turned on heating. Ins some instance the method includes communicating via illumination if the temperature of at least a portion of the common chamber is at a predetermined temperature.

A controller utilizing one or more temperature sensors maintains the chamber exposure temperatures (SET). SET is selected from the group consisting of about 180 degrees F., about 200 degrees F., about 220 degrees F., about 240 degrees F., about 260 degrees F., about 280 degrees F., about 300 degrees F., about 320 degrees F., about 340 degrees F., about 360 degrees F. about 380 degrees F., 390 degrees F., 400 degrees F., 410 degrees F., 420 degrees F., 430 degrees F., and 440 degrees F.

FIGURES

The invention may be better understood by referring to the following figures. The components in the figures are not necessarily to scale, emphasis instead being placed upon illustrating the principles of the invention. In the figures, like reference numerals designate corresponding parts throughout the different views.

FIGS. 10A-10D illustrate aspects of a two zone vaporizer.

FIG. 10E illustrates an airflow with fan zoned vaporizer.

FIG. 11A-11C illustrate aspects of a compact zoned vaporizer.

Figure 1A:
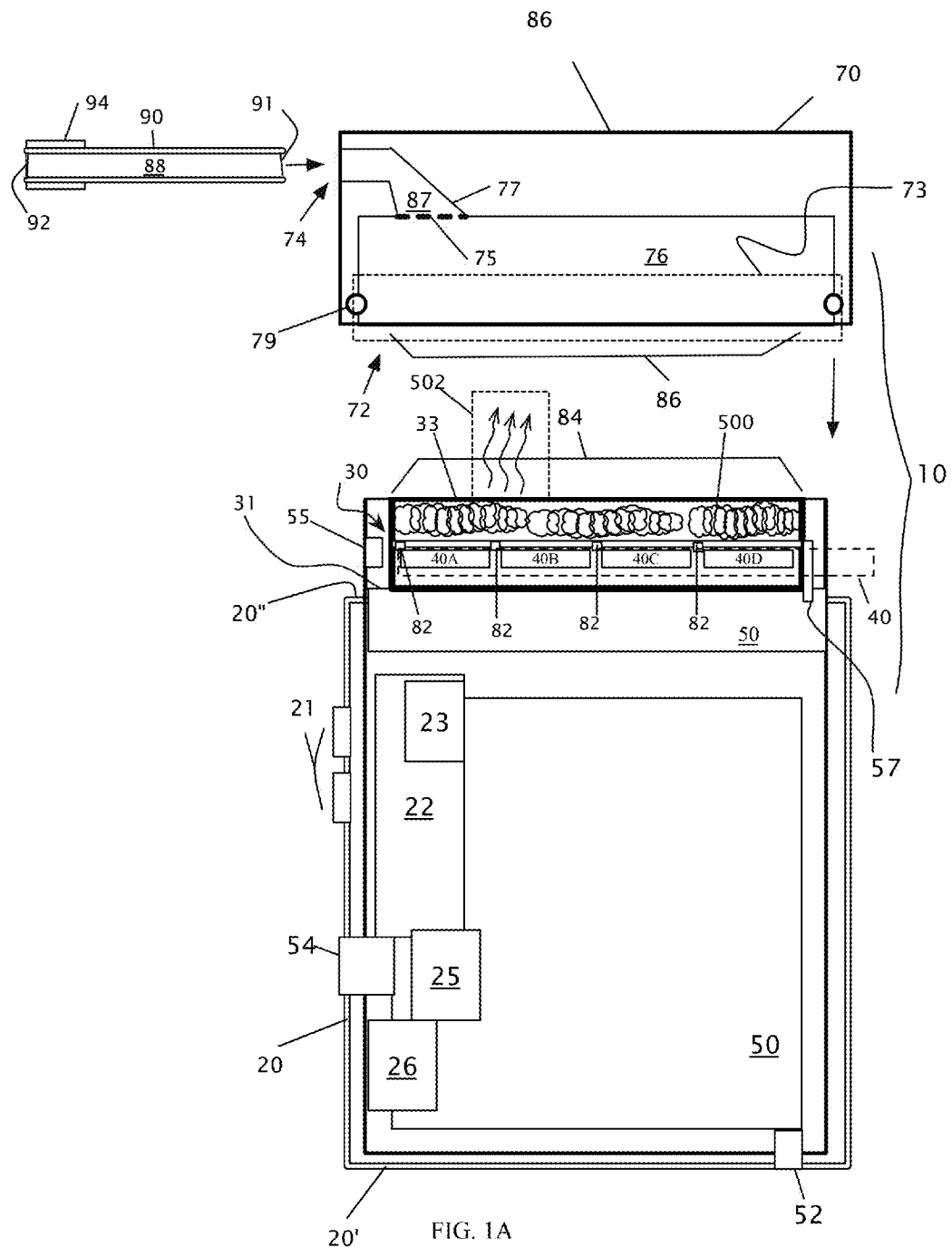
FIGS. 1A-1C illustrate aspects of a four zoned vaporizer.

All descriptions and callouts in the Figures and all content therein are hereby incorporated by this reference as if fully set forth herein.

Further Description

In the following description of examples of implementations, reference is made to the accompanying drawings that form a part hereof, and which show, by way of illustration, specific implementations of the present disclosure that may be utilized. Other implementations may be utilized and structural changes may be made without departing from the scope of the present disclosure.

Vaporizing plant material for aromatherapy is used to effect the olfactory receptors of a user, fill a room or a user's lungs with plant borne chemicals.

Aromatherapy and vaporization are considered by some to be less harmful then combusting the plant material. Tobacco and cannabis are examples of such material.

It is appreciated by those skilled in the art that some of the circuits, components, controllers, modules, and/or devices of the system disclosed in the present application are described as being in signal communication with each other, where signal communication refers to any type of communication and/or connection between the circuits, components, modules, and/or devices that allows a circuit, component, module, and/or device to pass and/or receive signals and/or information from another circuit, component, module, and/or device. The communication and/or connection may be along any signal path between the circuits, components, modules, and/or devices that allows signals and/or information to pass from one circuit, component, module, and/or device to another and includes wireless or wired signal paths. The signal paths may be physical such as, for example, conductive wires, electromagnetic wave guides, attached and/or electromagnetic or mechanically coupled terminals, semi-conductive or dielectric materials or devices, or other similar physical connections or couplings. Additionally, signal paths may be non-physical such as free-space (in the case of electromagnetic propagation) or information paths through digital components where communication information is passed from one circuit, component, module, and/or device to another in varying analog and/or digital formats without passing through a direct electromagnetic connection. These information paths may also include analog-to-digital conversions ("ADC"), digital-to-analog ("DAC") conversions, data transformations such as, for example, fast Fourier transforms ("FFTs"), time-to-frequency conversations, frequency-to-time conversions, database mapping, signal processing steps, coding, modulations, demodulations, etc. The controller devices and smart devices disclosed herein operate with memory and processors whereby code is executed during processes to transform data, the computing devices run on a processor (such as, for example, controller or other processor that is not shown) which may include a central processing unit ("CPU"), digital signal processor ("DSP"), additional memory may be added, application specific integrated circuit ("ASIC"), field programmable gate array ("FPGA"), microprocessor, etc. Alternatively, portions DCA devices may also be or include hardware devices such as logic circuitry, a CPU, a DSP, ASIC, FPGA, etc. and may include hardware and software capable of receiving and sending information.

A multi-zone vaporizer which controls heating of a sub-area or subzones within a heating chamber is disclosed. In some instance the control include software, logic and controllers having hardware, memory and microprocessors to control the zone heating and limit, warn about or prevent reheating of a used zone. In some instance the vaporizer includes BLUETOOTH®, WI-FI® or other wireless communication to a smart phone to allow an application on the smart phone to control heating of subzones. In some instance the vaporizer includes BLUETOOTH®, WI-FI® or other wireless communication to a smart phone to allow an application on the smart phone to control temperature settings.

Traditional portable vaporizers with single chamber heating may eventually burn some of the organic material therein. Repeated heating of a chamber from walls or floor surrounding the chamber can eventually dry out and burn the material after essential oils have been released. This problem includes the heating of cannabis plant material and cannabinoid containing concentrate.

Vaporizers provide a flow pathway from heating unit to inhalation path to user. The heat a chamber which may be high temperature plastic such as Dupont's VESPEL™, metal, ceramic or the like and within the chamber is placed organic material such a plant matter or concentrate which is heated to release vapor. Concentrate may be on a carrier substance. In many cases overheating causes some burning and charring.

For cannabinoids release of gas/vapor other than THC or CBDs in the cannabis material is suboptimal. The temperature range for release of many cannabinoids from cannabis plant material (and extracts) is about 170 degrees C. to about 215 degrees C.

The instant disclosure teaches a heater body having a rechargeable battery, a controller, memory, temperature sensor, open close lid sensor, a removable lid, a heating chamber, a fluid pathway to inhale vapor from, a heater vent, and an air intake vent. Also, disclosed is an on/off switch, indicator lights and a recharge connection. Further disclosed are communication interfaces with a user such as illumination which may turn on/off, flash and/or change color to communicate or indicate a state, or a change of condition to the user. Audible and/or tactile (vibration) communication is also disclosed. Finally a screen such as a LCD is disclosed.

In some instances the heater is a single heater placed or moved into proximity with the material in a chamber to vaporize wherein heat is supplied. In some instances a controller, such as a microprocessor with hardware and/or software logic turns on/off heating element. In some instance multiple heating elements are used to form zones to heat different sections of the chamber at different times.

The instant disclosure also teaches aspects of a zoned vaporizer with a fluid pathway for air to pass through organic material in a chamber being heated for vaporization. In some instances heater elements are arrayed or zoned and the controller or controllers turn heater elements on/off to apply heat to a selected portion or portions of the chamber. The controller may utilize a look up table in memory to determine parameters of the heating and/or timing of the heating of each zone.

Figure 1B:
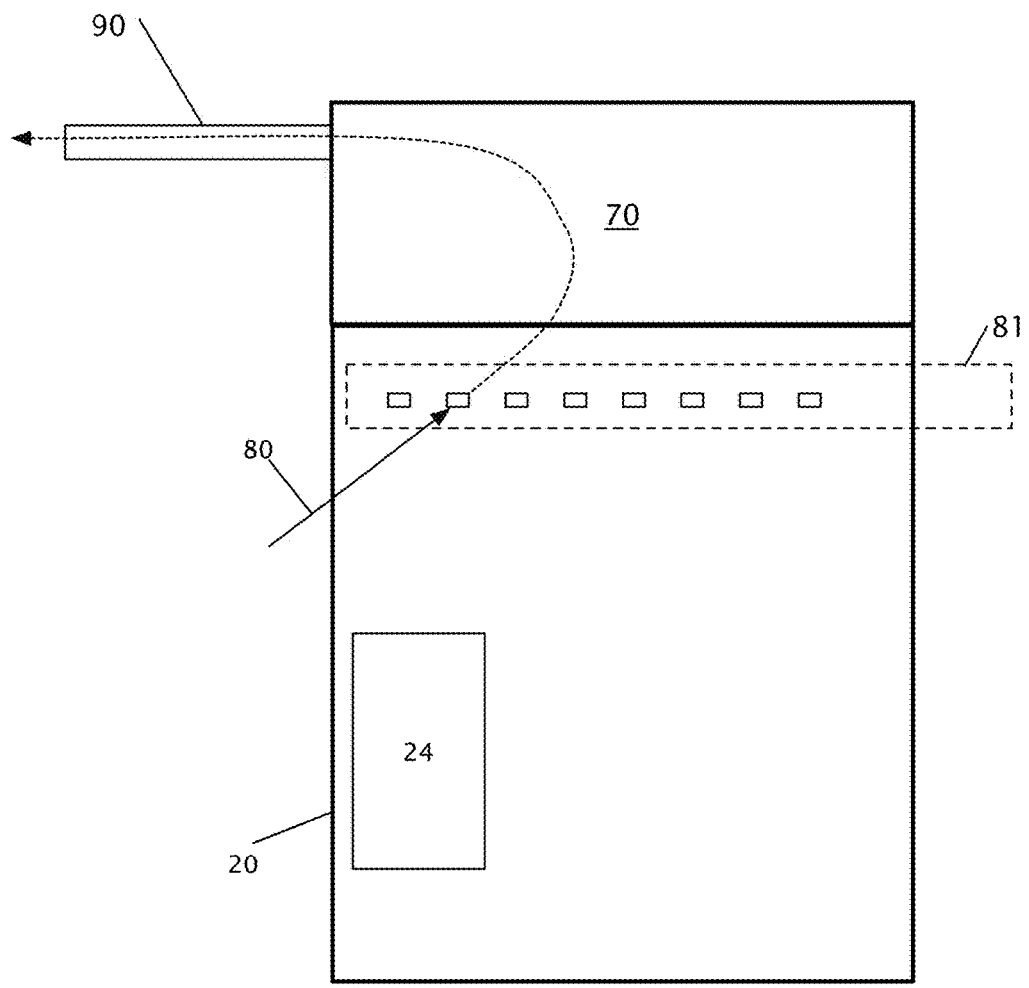
Figure 1C:
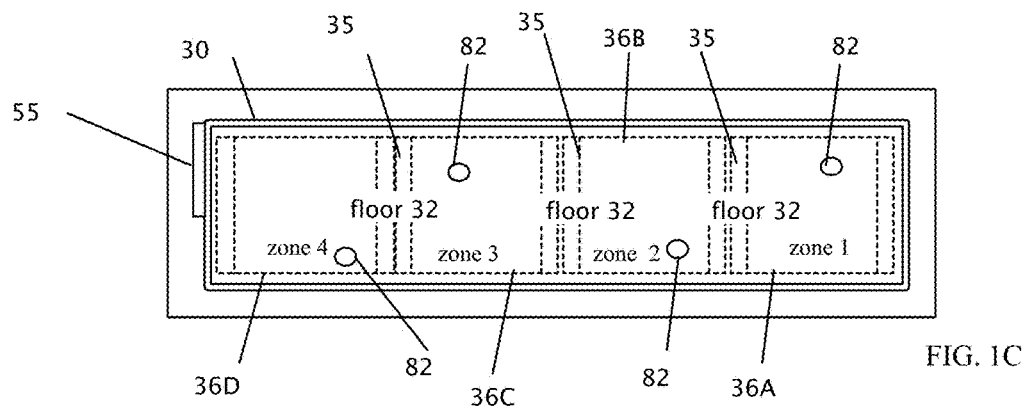

FIGS. 1A-1C discloses aspects of a vaporizer device 10 comprising an enclosure also referred to as a case 20 which may have one or more buttons 21 to communicate with a controller 22 which may have memory 23 therein. The enclosure is generally hollow it may have a closed bottom 20' and an open top 20" A communication display such as illumination via an electroluminescent screen, light emitting diode (LED) or a liquid crystal display 24 may be added, or communication with user may be via sound, or vibration. The case is covered with a removable lid. The case contains a heating chamber 30, with an annular wall 31, a floor 32 and an open top 33 which is in thermal communication with a heater system 40. In the heater system 40 are subzones. Subzone heating elements 40A-40D are in thermal contact with the floor 32 and may also wrap around the annular wall 31 to selectively apply heat as directed by the controller. A battery power supply 50 provides electricity to this portable device for functions of the controller, sensors, heater, and communications with user may be provided whereby a user can obtain status of the device or adjust settings. The battery power supply is at least one of rechargeable and replaceable. Insulation 505 may be added around the heater system 40. Within the chamber, zone insulation dividers 35 may be placed between the zones 36A-36D which are roughly above heating elements 40A-40D. The zone dividers may be flush with the floor, rise above the floor. Dividers may also be insulators to reduce thermal contact between material 500 in the regions or areas of the chamber.

A recharge connection 52 communicates through the enclosure or case for recharging the battery, it may be a USB or other power connection. Inside the case is a controller 22, optional I/O 54 may be a USB connector (or the like—THUNDERBOLT™) which may also provide recharging functions and data input/output. Additional memory via solid state device 25 may be provided. In some instances an optional wireless connection via WI-FI® 26 or BLU-ETOOTH®, WI-FI® or the like may be provide on the appropriate solid state device.

As part of the control system a lid on/off lid on/off sensor 55 can be provided. The sensor or actuator is a switch to interrupt power to the heater system if the lid is removed. The lid on/off can be used by the controller to reset the cycling of powering zone heaters when a lid has been removed after all zones have been heated for one of a fixed time, a variable time and a selected time. The selected time is selected by one of the user, a smart phone, and a controller. At least one temperature sensor 57 such as a thermistor or thermocouple is in close proximity to the heater system to communicate data to the controller whereby the energy provided to the heater system and zones is modulated to maintain a selected temperature. Wireless connection allows connecting the device to a smart phone which can have software (applications) which pair with the device 10 and adjust operation of the device via the controller.

Methods disclosed include a controller that manages heating of a zone at a selected exposure temperatures (SET) to vaporize a portion of the material in the containment area in the chamber accordance with one of variable, preselected and fixed times. The heating of all heating elements while the chamber contains material and without removing the lid may also be referred to as a cycle or a heating cycle. When a cycle is over the cycle has timed out. If the amount of time a specific heating element is to be heated is reached the heating of that element has timed out. The controller can track, monitor, measure or otherwise count that time.

In some instances the controller prohibits heating when a zone has already been heated for a predetermined time frame. In some instances the controller prohibits heating until the chamber has been refilled. In some instances the controller may accept a user over ride to allow reheating of a zone or to heat multiple zones simultaneously.

The case has a series of vents 81 which provide communication from the outside of the case to the inside. The lid 70 is removable, it has an open bottom 72 with an interface 73 for at least partially sealing off the top of the heating chamber and a interface for inhalation 74 which may be a mouth aperture, a screen 75 interposed between the inner cavity 76 of the lid and the outlet 77. An O-ring 79 or other seal may be interposed around the inner cavity to better seal the lid to the case. The device 10 provides a fluid inhalation pathway which draws outside air into the case through the chamber and out the lid. During aromatherapy inhalation when the heating system is activated, vapor from material 500 placed in the chamber is released and drawn through the fluid pathway to the user.

The fluid pathway 80 is limited by the apertures/vents of selected sizes and therefore can be used to roughly limit the amount of air that can be drawn by a inhalation of a predetermined force.

The fluid pathway starts with a series of vents 81 which provide communication from the outside of the case to the inside. A series of intakes 82 in the chamber 30 allow air to be drawn through the case into the chamber. The fluid pathway continues from the open top of the chamber 33 which forms a first fluid connection 84. The open bottom of the lid 72 forms a second fluid connection 86. The fluid pathway, in a assembled device, continues from the chamber through the first and second fluid connections and into the lid to the third connection 87 which is a fluid path in the outlet 77 and through the interface for inhalation 74. Optionally a generally tubular mouthpiece 90 with a first end 91 that mates with the interface 74 and a second end 92 for user inhalation can provide the exit path 88 for inhalation of fluid. In use, the heater system, heats up portions of the material 500 in the chamber and the vapors released therefrom 502 are moved through the fluid pathways of the device with the air which is moving through the fluid pathways during heating and inhalation. A flavor insert 94 may be added to the mouthpiece.

Figure 2:
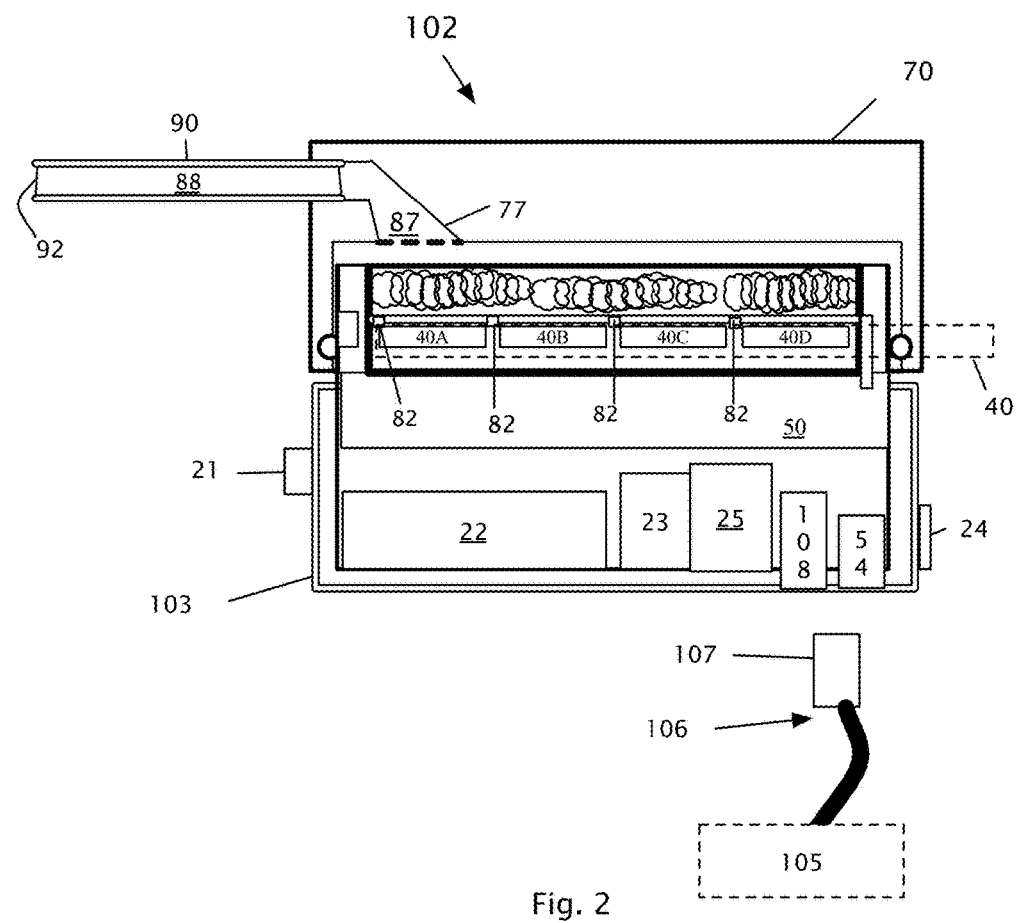
FIG. 2 illustrates a zoned heater system which uses remote power.
Figure 3:
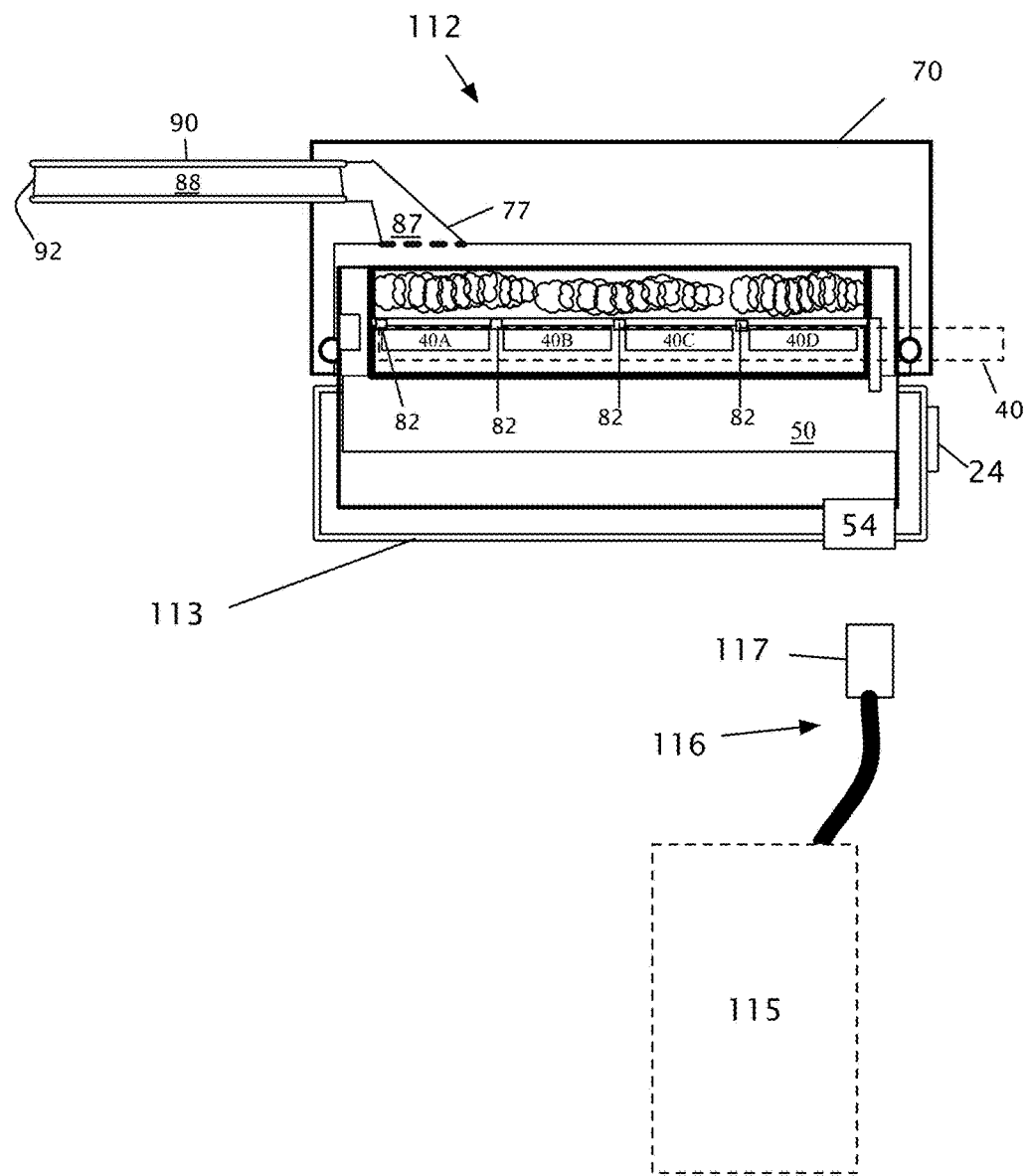
FIG. 3 illustrates a zoned heater system which uses remote controller and power.
Figures 4A, 4B:
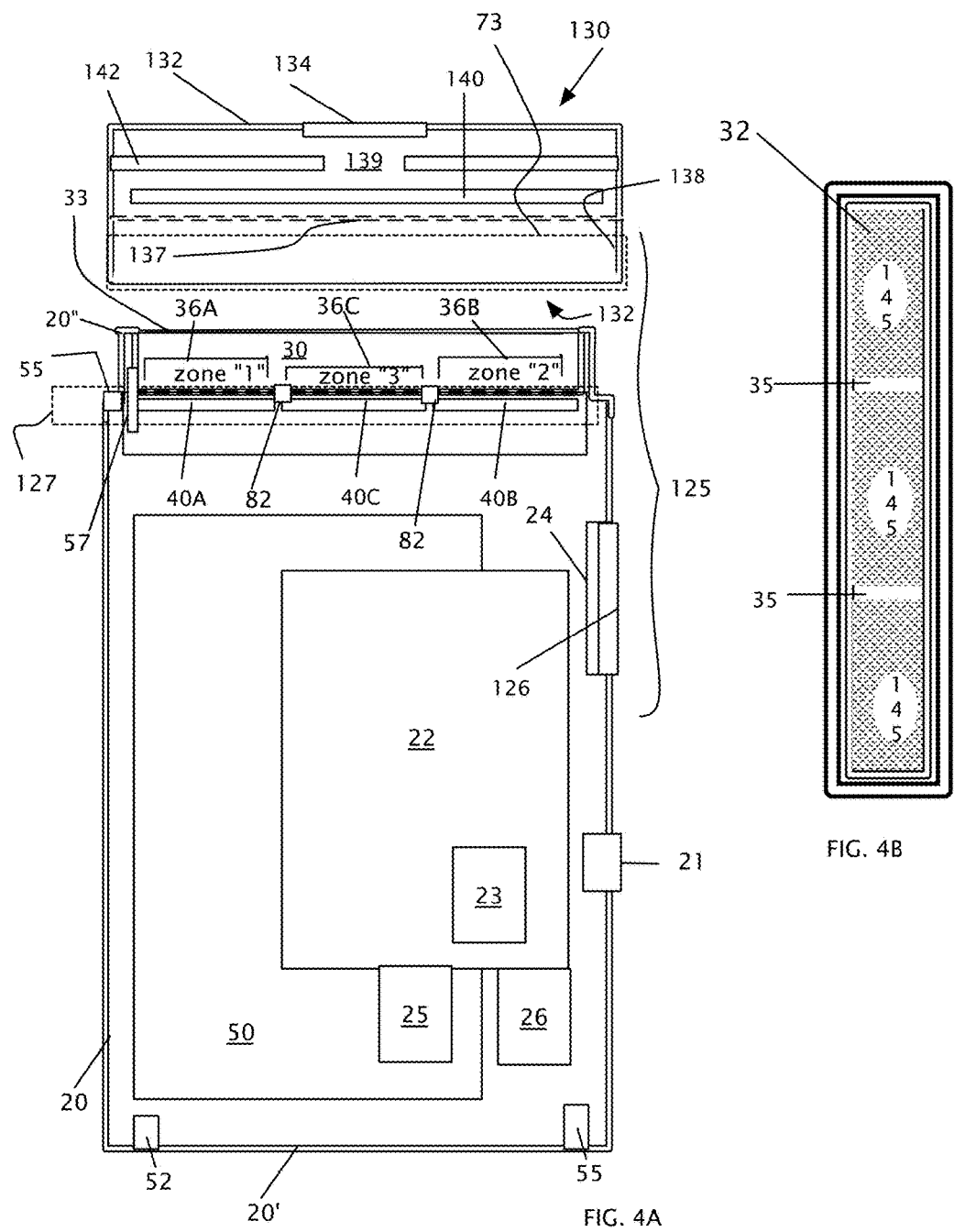
FIGS. 4A-4E illustrate aspects of a three zoned heating system.
Figure 4C:
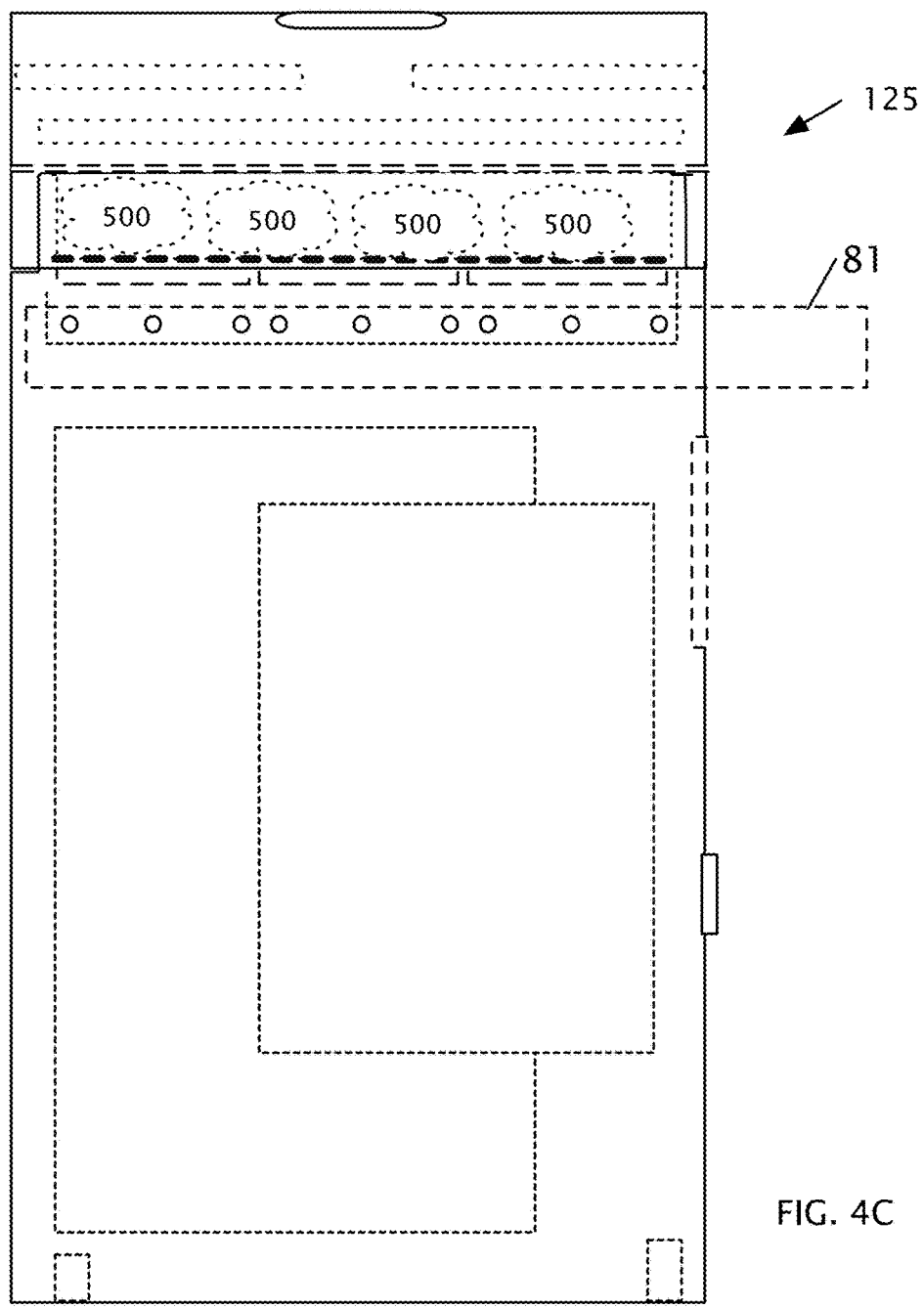
Figure 4D:
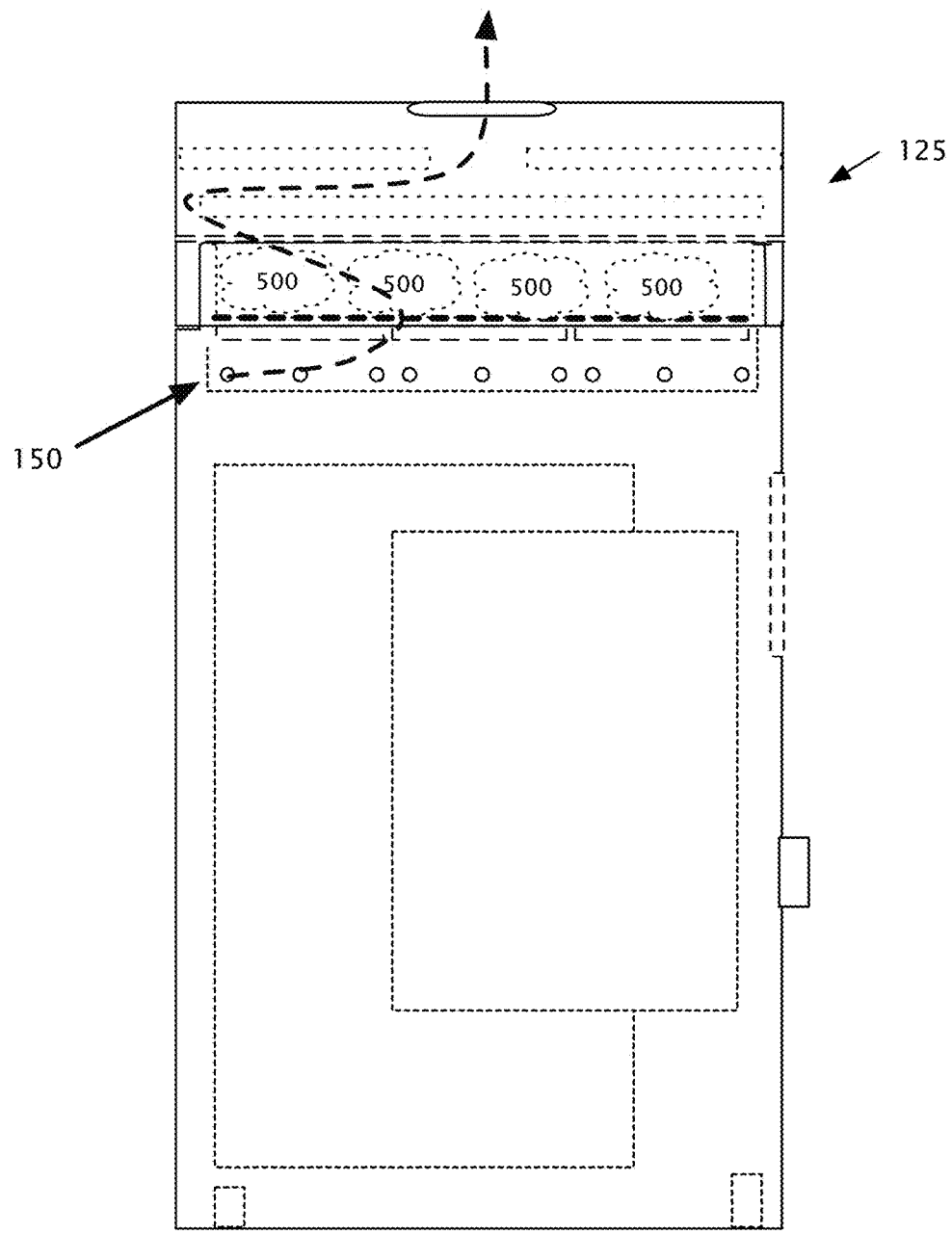
Figure 4E:
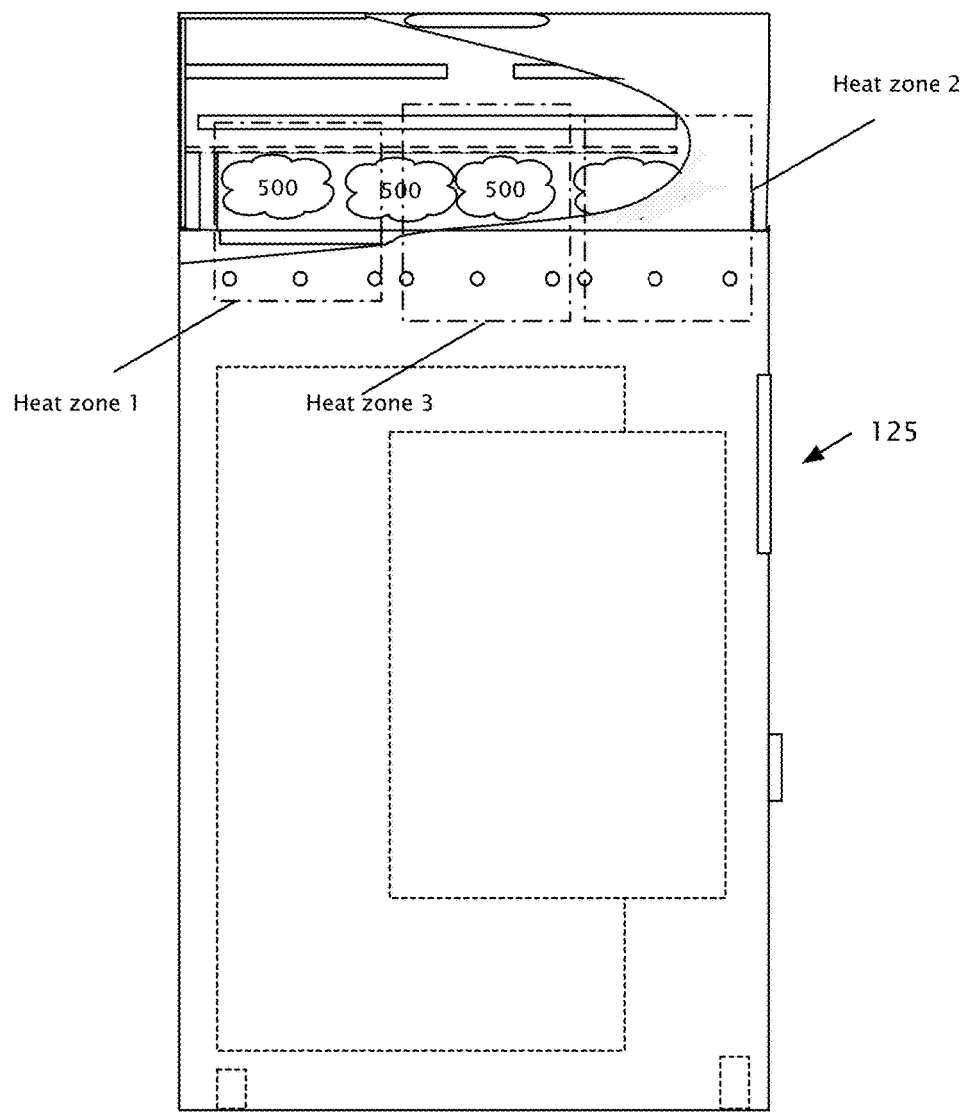
Figure 5A:
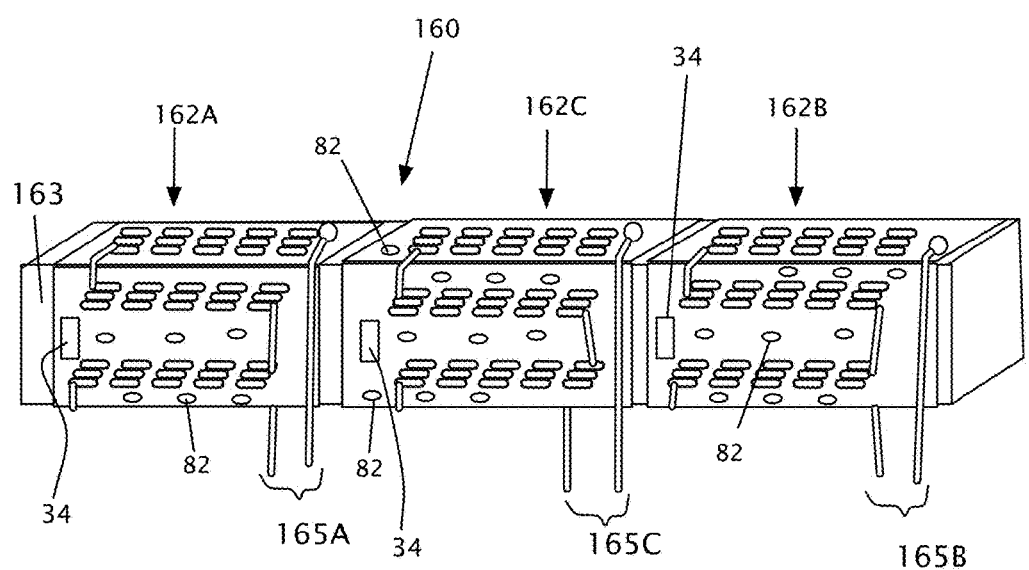
FIGS. 5A-5B illustrate a zoned conduction heating chamber and elements associated therewith.
Figure 5B:
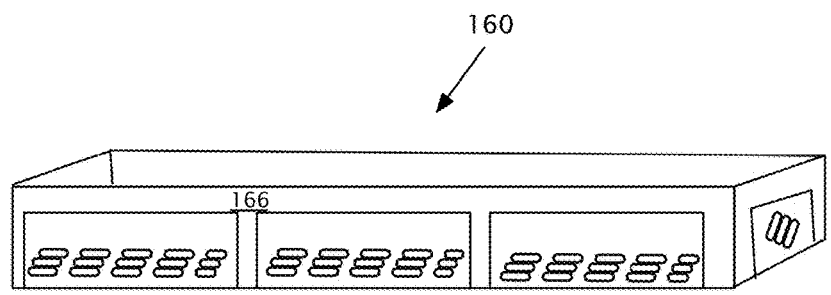

FIGS. 2 and 3 illustrate devices which utilize a similar multi zone heating system but leverage other devices for at least one of power and control. FIG. 2 illustrates a smart heating head device 102. It contains a heater system and lid with inhalation and fluid pathways as previously described however the case 103 does not contain a power suppl. The power supply 105 (such as lithium ion batteries, alkaline batteries, a fuel cell, or the like) is connected via a wired line 106 with a connector 107 that mates with a power input receptacle 108. The on/off switch 21 turns on the system and the controller 22 utilizes the remote but connected power supply to power the heating system. The controller and sensors control the device.

FIG. 3 illustrates a "dumb" heating head device 112. It contains a heater system and lid with inhalation and fluid pathways as previously described however the case 103 does not contain a power supply. The control and power supply device 115 (such as a smart phone) is connected via a wired line 116 with a connector 117 that mates with the I/) 54. The control and power supply device 115 turns on/off the heating system and via the sensors in the device 112 processes the data and controls the heating system.

FIGS. 4A-4E discloses aspects of a three zone vaporizer device 125 having a baffled cooling head lid. The device and system include a chamber for heating material. The chamber has a floor with vents that communicate into the chamber whereby heating elements in thermal communication with the chamber heat at least a portion of the chamber and material therein. A lid couples to or otherwise partially seals off the top of the heater chamber and also provides a fluid pathway from the partially sealed chamber to an intake passing from the lid whereby a user may inhale vapor for the material. The system may further comprise a case or enclosure 20 which may have one or more buttons 21 to communicate with a controller 22 which may have memory 23 therein. A communication display such as illumination via light emitting diode (LED) or a liquid crystal display 24 may be added, or communication with user may be via sound, or vibration. The case is covered with a removable lid. A translucent to transparent lens 126 may be added above the display and is useful to diffuse communication from an LED source. The case contains a common heating chamber 30, with an annular wall 31, a floor 32 and an open top 33 which is in thermal communication with a heater system 127. In the heater system 40 are subzones. Subzone heating elements 40A-40C are in thermal contact with the floor 32 and may also wrap around the annular wall 31 to selectively apply heat as directed by the controller. The heating zones 36A-36C are offset as part of a method of heating. Zone "1" (36A) is on one side of the chamber above a first heating element 40A. Zone "2" (36B) is at the other side of the chamber above the second heating element 40B. In between zone "1" and zone "2" is zone "3" (36C) above heating element 40C. By heating the two side zones and then the center zone the local heat is separated by physical space avoiding some heat spill over from heating zone "1" into heating zone "2" which in turn may preserve more of the cannabinoids that remain in zone "2" for the next usage. If all zones are heated at the same time cannabinoids which vaporize at lower the 400 F degrees will be vaporized during the initial heating and inhalation thereby providing less of these potentially beneficial cannabinoid in subsequent inhalations or for second or third users sharing a device. The communication display may indicate to a user if the device is active, ready for inhalation, needs a recharge, needs a refill of material or is still heating at least a portion of the common chamber.

The case has a series of vents 81 which provide communication from the outside of the case to the inside. The lid 130 is removable, it has an open bottom 132, an interface 73 and an outlet 134 for inhalation, a screen 137 is interposed between the case interface 138 of the lid and the fluid cavity 139. A series of baffles 140 & 142 are formed within the fluid cavity 139 whereby the fluid pathway 150 from the exterior of the case, through the vents 81 to the user is direct in part by the baffles. The floor of the camber 145 may be substantially permeable to airflow such as a fine mesh, a metal or ceramic foam, or a series of laser drilled apertures.

FIGS. 5A-6C illustrate variations on a zoned heating chamber using induction or conduction heater elements in close proximity to the exterior annular wall of the heating chamber.

Chamber 160 is generally elongated, although shown as rectangular those of ordinary skill in the art will recognize that adding a radius to the corners and a draft angle or slope to the walls is within the scope of the disclosure. Air flow into the chamber is through intake vents 82. The zoned heating utilizes separate heating elements 162A-C. The elements are in thermal contact with the annular wall 163 of the chamber. Each heating element has electrical contacts 165A-C which are connected to the controller (not shown) whereby the zone that is being heated. A heated zone with a heating element receiving electrical power may be referred to as active because it is receiving power and therefore turned on. Temperature sensors 34 such as thermistors and thermocouples are placed near each zone heater and are electrically connected to the controller (not shown). The heating elements 162A-C may wrap around the sides 166 of the annular wall. The measurement of heat derived from the temperature sensor data is used by the controller to adjust the electricity provided to an active heating element to target a predefined temperature or range of temperatures.

Chamber 170 is generally elongated, although shown as rectangular those of ordinary skill in the art will recognize that adding a radius to the corners and a draft angle or slope to the walls is within the scope of the disclosure. The chamber may be constructed of metal, ceramic, high temperature plastic, it may be metallized plastic, formed of glass such as quartz glass or borosilicate. A shaped chamber may have thickened sections which form part of the insulator dividers 35 (which are optional).

Figure 6A:
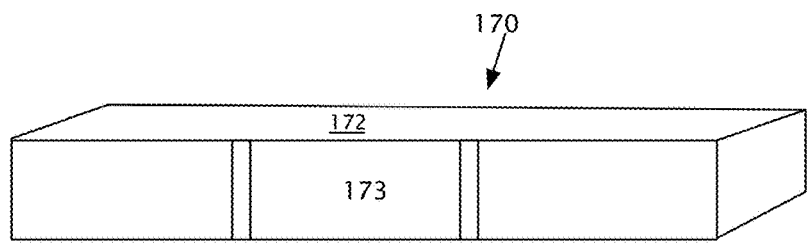
FIGS. 6A-6C illustrate a zoned conduction heating chamber and elements associated therewith.
Figure 6B:
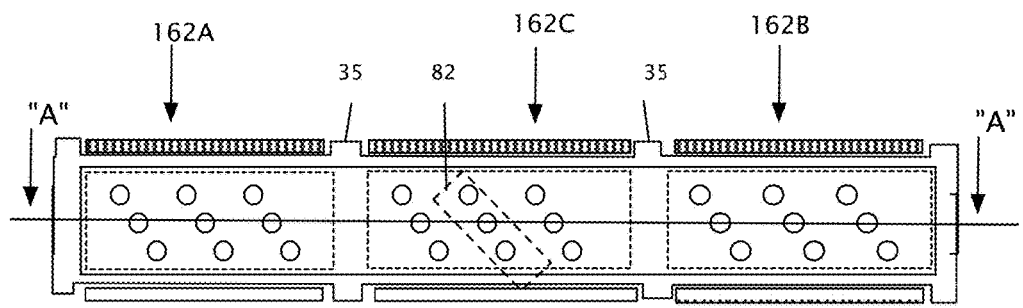
Figure 6C:
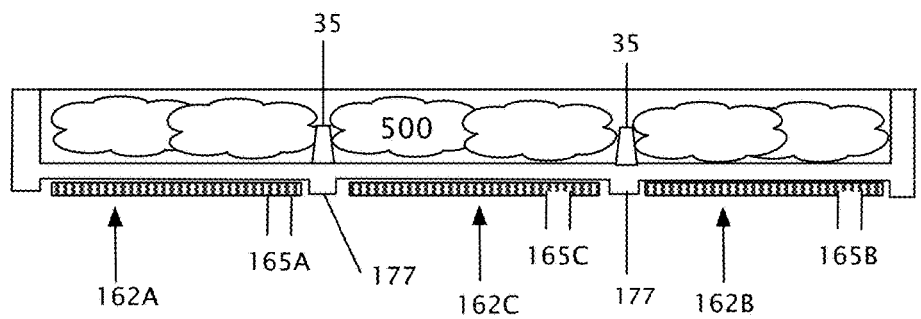

FIG. 6A is a bottom perspective view of the chamber, FIG. 6B is bottom view of the chamber. FIG. 6C is a cut-away view along the line of "A"-"A" of FIG. 6B. Air flows into the chamber 170 through intake vents 82. The zoned heating utilizes separate heating elements 162A-C. The elements are in thermal contact with the annular wall 172 of the chamber. Each heating element has electrical contacts 165A-C which are connected to the controller (not shown) whereby the zone that is being heated is turned on and off and the temperature thereby is adjusted. Temperature sensors 34 such as thermistors and thermocouples are placed near each zone heater and are electrically connected to the controller (not shown). The heating elements 162A-C may wrap around the sides 173 of the annular wall. Extended heat sinks or cooling fins 177 may be formed as part of the chamber or affixed thereto to assist with heat management in the chamber and zones.

Figure 7:
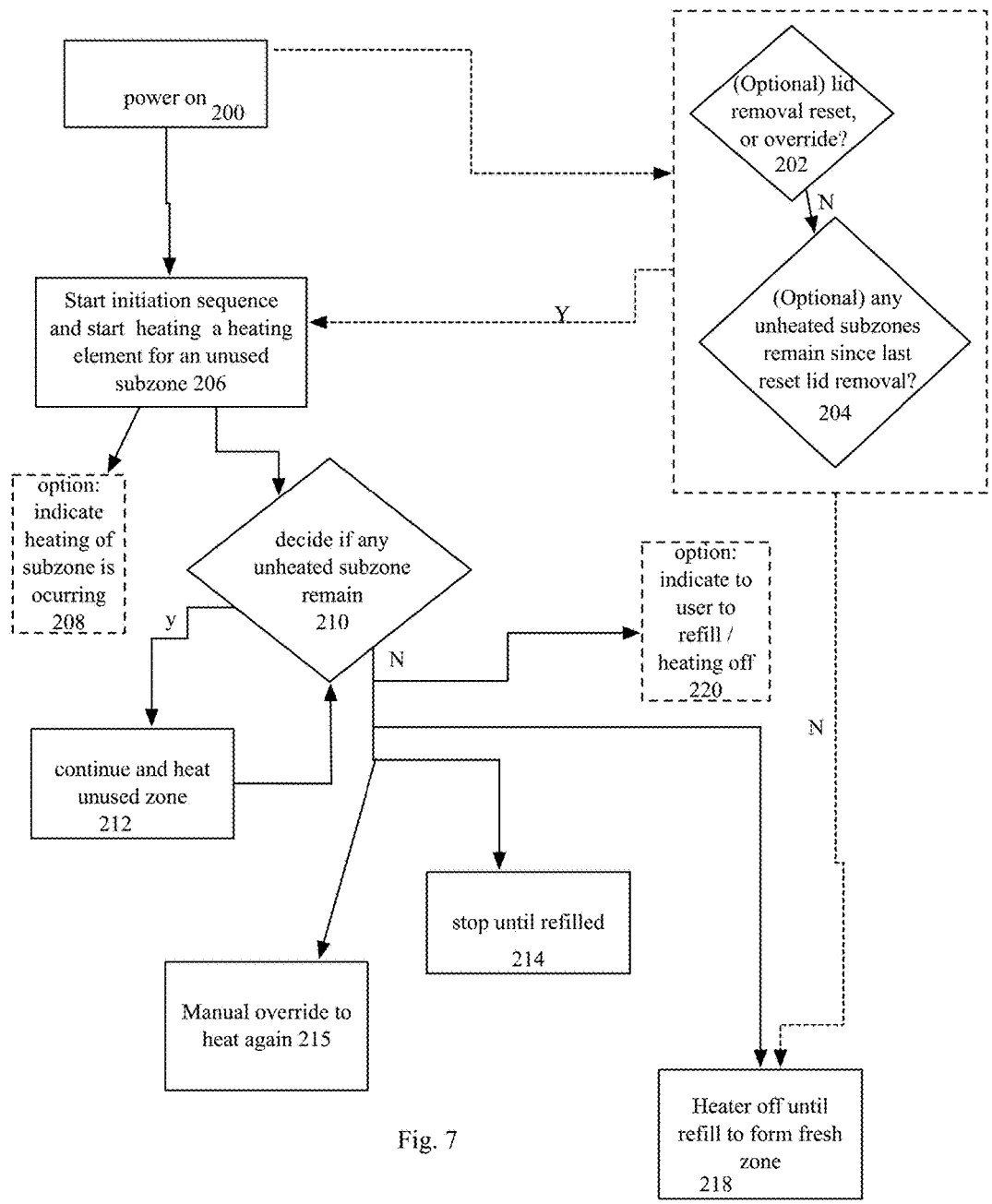
FIG. 7 illustrates some of the electrical and control connects to the controller.

FIG. 7 is a process diagram of aspects of controller logic for a vaporizer. Power is turned on 200 for the device. Optional determine if heating chamber has gone through a full cycle of heating all subzones without lid/cover removal or user override 202, if not, then optionally decide if any unheated zones remain 204. Next, start an initiation sequence to heat a heating element for an unused subzone 206. Optionally, indicate via indicator light to user that heating is occurring 208. Determine if any unheated heat subzones remain 210. If unheated subzone remains heat an unused subzone 212. If all heating subzones have been used stop 214. Turn heating elements off and do not heat until confirmation of refill, such as lid removal, or a user override to have one last attempt to extract additional vapor by reheating used subzones either individually or as a group 215. After heating a heating subzone determine if the heating sequence has heated all heating zones and is complete 210. If completed sequence turn off heating until lid removed for refill 218. If sequence is complete and heating of subzones is stopped indicate to user via indicator lights 220.

Figure 8:
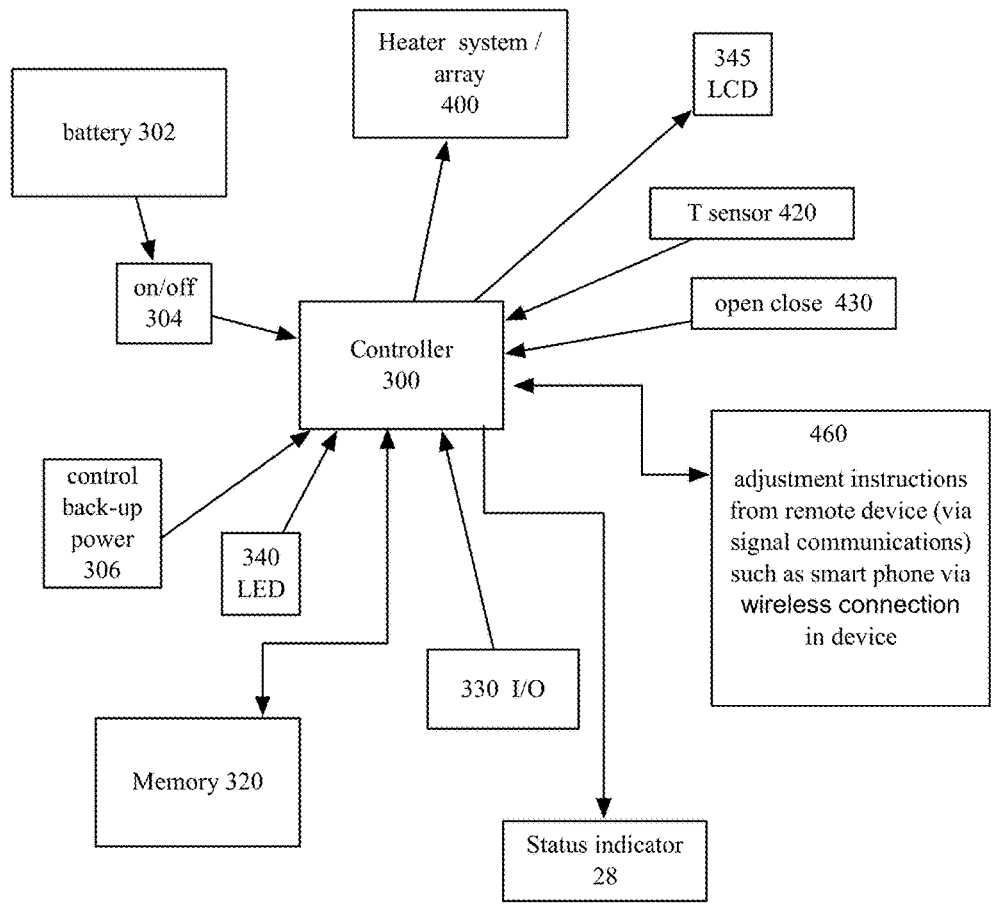
FIGS. 8 and 9 illustrates aspects of control logic of zoned heating.
Figure 9:
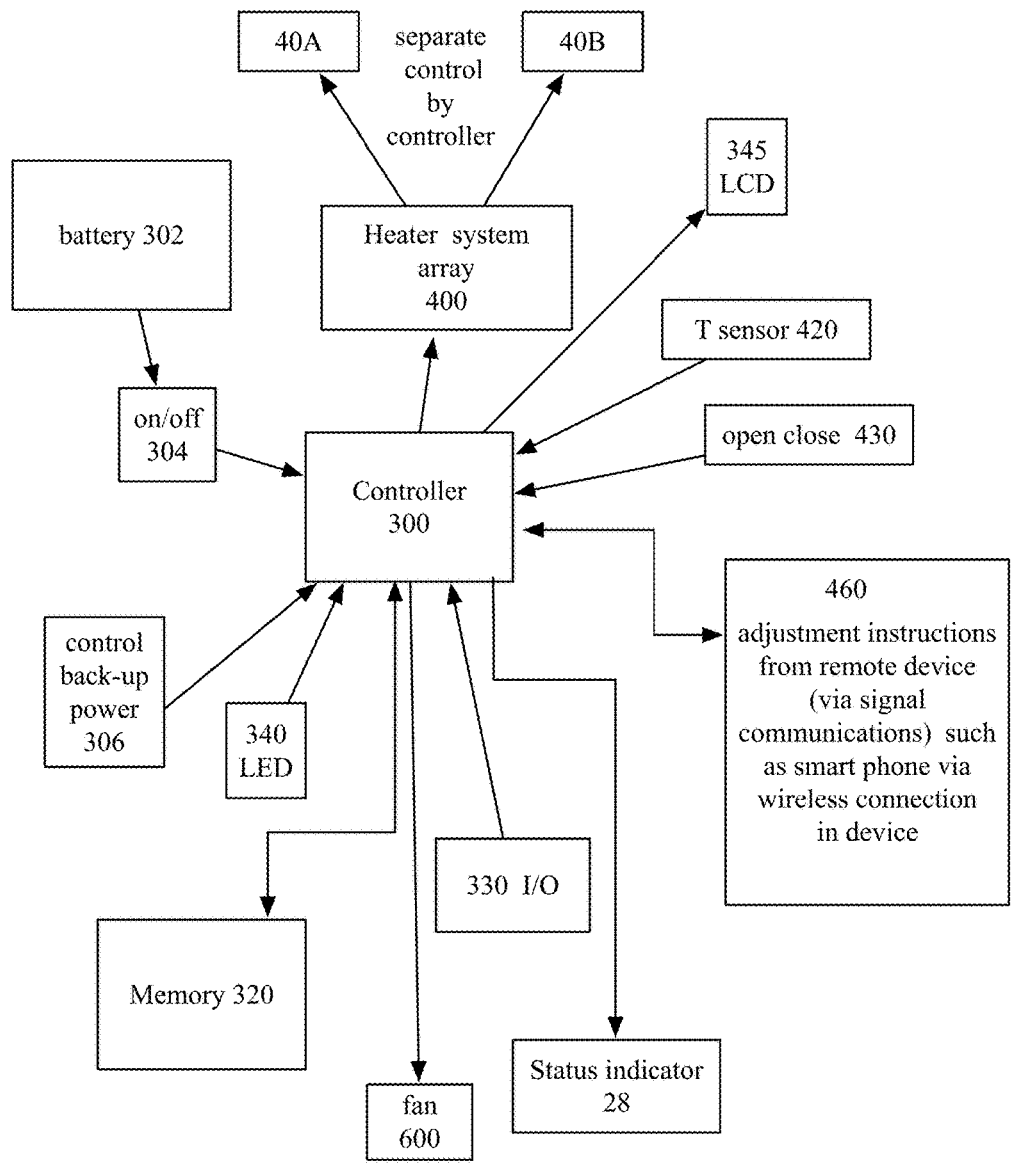

FIGS. 8 and 9 shows a aspects of control systems. A controller 300 in electrical and/or signal communication with other system sensors and components. The battery 302 to power the controller and the device is connected to an on/off switch 304 wherein power is supplied to the controller. Optionally the system may have a back-up battery power supply 306 which supplies power to the controller or other components when the main battery (302) is disconnected. Alternatively memory either volatile or non-volatile will store data on system parameters when the controller is not powered. The controller instructs the on/off of heating elements in the heating system 400. In some instances the heating of heating elements 40A and 40B are separately controlled by the controller. The controller controls the electrical power supplied to the heating element(s) from the power supply (302). One or more temperature sensors 420 provide temperature measurements to the controller. A open/close sensor 430 is used to determine if the lid of the device has been removed and may be used to reset the initiation sequence based on assumptions such as an opened lid equates to a refilled heating chamber. The controller can be in signal communications with memory 320. Communication between a computer or smart phone with the controller may be via an input/output 330. Input to the controller may also be via the input buttons 332 and a status indicator such as a colored LED communication illumination 340 and/or an LCD 345 type display can show a setting such as the heat setting for the heating chamber or the length of time of each heating cycle. The LCD 345 and the status indicator 340 are controlled by the controller whereby a status such as heating a heating element is indicated or system has determined the zones have all been heated and heating has been stopped, or the device needs to be recharged. In some instances the controller may receive adjustment instructions via a computing device of smart phone in wireless signal communication with the controller 460.

FIGS. 10A-11C discloses aspects of a vaporizer devices 10 comprising an enclosure also referred to as a case 20 which may have one or more user interfaces, such as press or push buttons or switches 21 to communicate with a controller 22 which may have memory therein. The enclosure is generally hollow it may have a closed bottom 20' and an open top 20" A communication display such as illumination via an electroluminescent screen, light emitting diode (LED) or a liquid crystal display may be added, or communication with user may be via sound, or vibration. The case has an open top 20" hat is sealed with a removable lid. The case contains a heating chamber 30, with an annular wall 31, a floor 32 and an open top 33 which is in thermal communication with a heater system 40. In the heater system 40 are subzones which are independently controlled by the controller whereby heat is generated via the use of electrical power. Resistance type heaters which may be one or more of around or within materials such as ceramic walls are examples of heating elements. Subzone heating elements 40A-40B are in thermal contact with the floor 32 and may also wrap around the annular wall 31 of each zone 36A and 36B to selectively apply heat as directed by the controller. A battery power supply 50 provides electricity to this portable device for functions of the controller, sensors, heater, and communications with user may be provided whereby a user can obtain status of the device or adjust settings. The battery power supply is at least one of rechargeable and replaceable. The heating elements are configured to receive electrical power. The controller is configured to control the supply of electrical power to the heating elements and that control may be via pulse width modulation. Insulation 505 may be added around the heating chamber 30 and heater system 40. Within the chamber, zone insulation divider 35 is interposed between zones to thermally separate at least a portion of zone 36A and 36B. In some instances the insulator may be a ring between two cylindrical portions or units forming the heater system 40. The insulator divider separates zone 36A and 36B. The insulation divider 35 reduces thermal communication between zones by dividing thermal contact between the annular wall 31 of the chamber heated by one of heating element 40A and 40B and the annular wall of the portion of the chamber not being heated by a heating element. The zone divider may be flush with the floor, rise above the floor and/or divide portions of the annular wall 31. Divider may also be insulators to reduce thermal contact between material 500 in the regions or areas of the chamber.

A recharge connection 52 communicates through the enclosure or case for recharging the battery, it may be a USB or other power connection. Inside the case is a controller 22, optional I/O 54 may be a USB connector (or other standard such as USB-C, micro USB and the like) which may also provide recharging functions and data input/output. Additional memory via solid state device may be provided. In some instances an optional wireless connection via Wi-Fi or Bluetooth or the like may be provide on the appropriate solid state device.

At least one temperature sensor 57, for the chamber or in other instances one temperature sensor 57 per zone 36A and 36B. (a first and a second sensor) such as a thermistor or thermocouple is placed in close proximity to the heater system to communicate data to the controller whereby the energy provided to the heater system and subzones is modulated to maintain a selected temperature. Wireless connection allows connecting the device to a smart phone which can have software (applications) which pair with the device 10 and adjust operation of the device via the controller.

In some exemplars the chamber 30 is formed as a pass-through with both an open top 33 and an open bottom 33". A case closure 37 mates with the bottom of the case 20B. Inside the case closure is a chamber closure interface which supports a removable floor 32 that seals the bottom of the chamber and provides a fluid pathway for air to be drawn into the chamber. The case closure 37 provides a series of vents 81 which communication from the outside of the case to the inside. A series of intakes 82 create a fluid pathway into the chamber 30 allow air to be drawn through the case vents 81 and into the chamber.

The fluid pathway starts with the series of vents 81 which provide communication from the outside of the case to the inside. A series of intakes 82 in the chamber 30 allow air to be drawn through the case vents 81 and into the chamber. The fluid pathway continues from the open top of the chamber 33 into the open bottom of the lid 72 through the fluid pathway 80 to an interface for inhalation 74 at one end of the fluid pathway. In some instances an optional mouthpiece 90 may be added to the fluid pathway. To help clear used material from the chamber a user may remove the case closure and exhale 510 through the fluid pathway to urge the spent material our the open bottom 33" of the chamber.

Methods disclosed include a controller that manages heating of a zone at a selected exposure temperatures (SET) to vaporize a portion of the material in the containment area in the chamber accordance with one of variable, preselected and fixed times. The heating of all heating elements while the chamber contains material and without removing the lid may also be referred to as a cycle or a heating cycle. When a cycle is over the cycle has timed out. Temperature sensors are utilized to measure when the chamber or subzone has reached a target temperature. If the amount of time a specific heating element is to be heated is reached the heating of that element has timed out. The controller can track, monitor, measure or otherwise count that time. In other instances the controller may switch between subzones, preferably using a PWM protocol to supply power to each heating element separately to maintain an overall temperature in each chamber at a predetermined range.

The case has a series of vents 81 which provide communication from the outside of the case to the inside. The lid 70 is removable, it has an open bottom 72 with an interface 73 for at least partially sealing off the top of the heating chamber and a mouth aperture 74 for inhalation. The interface 73 mates with a chamber interface 73' formed at the open top 33 of the chamber 30. Baffles—may be added within the lid to lengthen the fluid pathway of vapor passing into the lid. The device 10 provides a fluid inhalation pathway which draws outside air into the case through the chamber and out the lid. During inhalation, when the heating system is activated vapor from material 500 placed in the chamber is released and drawn through the fluid pathway to the user during the inhalation.

The fluid pathway starts with a series of vents 81 which provide communication from the outside of the case to the inside. A series of intakes 82 in the chamber 30 allow air to be drawn through the case vents 81 and into the chamber. The fluid pathway continues from the open top of the chamber 33 into the open bottom of the lid through the interface for inhalation 74.

In some instances the controller prohibits heating when a zone has already been heated for a predetermined time frame. In some instances the controller prohibits heating until the chamber has been refilled. In some instances the controller may accept a user over ride to allow reheating of a zone or to heat multiple zones simultaneously.

FIG. 10E provides an electrical fan 600 which is in fluid connection 605 with the intakes 82 at the bottom of the chamber 30. The fan 600 is in signal communication with the controller and may be activated by depression of the on/off switch whereby air is drawn into the device and expelled through the interface for inhalation 74 via the fan. In some instances a use controlled switch (not shown) may act as an on/off for the fan.

It will be understood that various aspects or details of the disclosures may be changed combined, or removed without departing from the scope of the invention. It is not exhaustive and does not limit the claimed inventions to the precise form disclosed. Furthermore, the foregoing description is for the purpose of illustration only, and not for the purpose of limitation. Modifications and variations are possible in light of the above description or may be acquired from practicing the invention. The claims and their equivalents define the scope of the invention.

What is claimed is:

1. A vaporizer system comprising:
    a controller;
    a battery power supply;
    an on/off switch;
    a heating chamber comprising;
    an open top (33) surrounded by an annular wall and having an open bottom (33");
    a floor (32) having at least one air intake (82) there through;
    vents in at least one of the annular wall and the floor;
    at least two or more heating elements each in thermal contact with a portion of the heating chamber;
    a divider (35) between the portions of the heating chamber;
    a resealable lid (70) which reversibly mates with the heating chamber;
    a fluid pathway (80) inside the lid from the top of the open chamber to an interface for inhalation (74);
    wherein each heating element is separately controlled by the controller;
    wherein the floor closes off a portion of the bottom of the heating chamber and is one of fixed to the open bottom or removable from the open bottom; and,
    wherein the power supply is electrically connected to the heating elements and the controller via the on/off switch.

2. The vaporizer system of claim 1, wherein the divider is an insulator.

3. The vaporizer system of claim 1, further comprising at least one temperature sensor (57).

4. The vaporizer system of claim 1, further comprising a fan (600) which directs air into the vents on said floor.

5. The vaporizer system of claim 4 wherein the temperature sensor is connected to the controller and the controller in response to temperature sensor measurements adjusts the amount and/or timing of electricity provided to a turned-on heating.

6. The vaporizer system of claim 1 further comprising an illumination (340) communications system controlled by the controller.

7. The vaporizer system of claim 1 further comprising a case (20) surrounding at least the heating chamber.

8. The vaporizer system of claim 1 wherein the controller at least one of measures the amount of time a heating element is at a predetermined range of temperature and measures when a predetermined time is met.

9. The vaporizer system of claim 8 wherein the controller determines if a zone or heating element has measured at a predetermined temperature for a predetermined amount of time.

10. The vaporizer system of claim 9 further comprising a sensor which measured one or more of when the lid is place on the chamber and when the lid is removed from the chamber.

11. The vaporizer system of claim 1 wherein the controller controls heat to each zone heating element based on one of a fixed time, a variable time and a selected time.

12. The vaporizer system of claim 1 wherein the fluid pathway in the lid further comprises one or more baffles to direct the flow of vapor.

13. An aromatherapy method, the method comprising:
    encasing (20) a generally tubular heating chamber (30) having two or more heating zones (36A-36B) each zone having a heating element (40A-40B) configured to receive electrical power from one at least one of a battery power supply and controller;
    temporarily and partially closing off an open bottom 33" of the tubular chamber with a floor;
    placing material (500) in to an open top (33) of the chamber;
    covering the open top of the tubular chamber with a lid having a fluid pathway from the open top through the lid to an interface for inhalation (74);
    wherein each heating element is separately controlled by the controller;
    wherein the power supply is electrically connected to the heating elements and the controller via a user activated on/off switch controls the supply of power to each of the heating elements; and,
    wherein the controller supplies sufficient electrical power to the heating element to vaporize at least some of the essential oils of the material.

14. The aromatherapy method of claim 13 wherein the controller will not provide electricity for a heating element until such time as the lid is covering the open top of the chamber.

15. The aromatherapy method of claim 13 wherein the controller stops providing electrical power to a heating element after a predetermined amount of time.

16. The aromatherapy method of claim 15 wherein the controller will not provide heating for any heating element after the time is met until such time as the lid has been removed from the chamber.

17. The aromatherapy method of claim 13, further comprising:
    at least one temperature sensor in signal communication with the controller; and, wherein the controller in response to temperature sensor measurements adjusts the amount and/or timing of electricity provided to a heating element.

\* \* \* \* \*